(12) United States Patent
Wang et al.

(10) Patent No.: US 8,592,641 B2
(45) Date of Patent: *Nov. 26, 2013

(54) WATER-SENSITIVE BIODEGRADABLE FILM

(75) Inventors: James H. Wang, Appleton, WI (US); Bo Shi, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 664 days.

This patent is subject to a terminal disclaimer.

(21) Appl. No.: 11/640,109

(22) Filed: Dec. 15, 2006

(65) Prior Publication Data

US 2008/0147034 A1 Jun. 19, 2008

(51) Int. Cl.
*A61F 13/15* (2006.01)
*A61F 13/20* (2006.01)

(52) U.S. Cl.
USPC ....... 604/364; 604/358; 604/385.05; 523/111

(58) Field of Classification Search
USPC .................. 524/47; 604/364, 370, 367, 372; 428/41.8
See application file for complete search history.

(56) References Cited

U.S. PATENT DOCUMENTS

| | | | |
|---|---|---|---|
| 3,071,485 A | 1/1963 | Wurzburg et al. | |
| 3,243,308 A | 3/1966 | Barger et al. | |
| 3,354,506 A | 11/1967 | Raley | |
| 3,575,173 A | 4/1971 | Loyer | |
| 3,650,649 A | 3/1972 | Schippers | |
| 3,801,429 A | 4/1974 | Schrenk et al. | |
| 4,333,464 A | 6/1982 | Nakano | |
| 4,499,154 A | 2/1985 | James et al. | |
| 4,503,098 A | 3/1985 | Potts | |
| 4,789,699 A | 12/1988 | Kieffer et al. | |
| 4,798,603 A | 1/1989 | Meyer et al. | |
| 4,801,494 A | 1/1989 | Datta et al. | |
| 4,886,512 A | 12/1989 | Damico et al. | |
| 4,908,026 A | 3/1990 | Sukiennik et al. | |
| 4,964,857 A | 10/1990 | Osborn | |
| 5,073,455 A | 12/1991 | Nose et al. | |
| 5,106,890 A | 4/1992 | Maruhashi et al. | |
| 5,196,247 A | 3/1993 | Wu et al. | |
| 5,217,803 A | 6/1993 | McBride et al. | |
| 5,219,646 A * | 6/1993 | Gallagher et al. | 442/361 |
| 5,248,309 A | 9/1993 | Serbiak et al. | |
| 5,254,607 A | 10/1993 | McBride et al. | |
| 5,292,783 A * | 3/1994 | Buchanan et al. | 524/37 |
| 5,300,358 A | 4/1994 | Evers | |
| 5,346,936 A | 9/1994 | Buehler et al. | |
| 5,350,354 A | 9/1994 | Billmers | |
| 5,362,777 A * | 11/1994 | Tomka | 524/47 |
| 5,405,564 A | 4/1995 | Stepto et al. | |
| 5,412,005 A | 5/1995 | Bastioli et al. | |
| 5,415,643 A | 5/1995 | Kolb | |
| 5,416,181 A | 5/1995 | Nguyen et al. | |
| 5,436,078 A | 7/1995 | Bühler et al. | |
| 5,446,079 A * | 8/1995 | Buchanan et al. | 524/41 |
| 5,452,981 A | 9/1995 | Crorey et al. | |
| 5,462,981 A | 10/1995 | Bastioli et al. | |
| 5,506,277 A | 4/1996 | Griesbach, III | |
| 5,509,913 A | 4/1996 | Yeo | |
| 5,525,281 A | 6/1996 | Lörcks et al. | |
| 5,558,659 A | 9/1996 | Sherrod et al. | |
| 5,559,171 A | 9/1996 | Buchanan et al. | |
| 5,565,509 A | 10/1996 | Nguyen et al. | |
| 5,580,911 A | 12/1996 | Buchanan et al. | |
| 5,599,293 A | 2/1997 | Orenga et al. | |
| 5,599,858 A | 2/1997 | Buchanan et al. | |
| 5,649,916 A | 7/1997 | DiPalma et al. | |
| 5,662,731 A | 9/1997 | Andersen et al. | |
| 5,665,786 A | 9/1997 | Xu et al. | |
| 5,679,145 A | 10/1997 | Andersen et al. | |
| 5,681,299 A | 10/1997 | Brown | |
| 5,695,868 A | 12/1997 | McCormack | |
| 5,700,553 A | 12/1997 | Cohen et al. | |
| 5,722,966 A | 3/1998 | Christon et al. | |
| 5,759,569 A | 6/1998 | Hird et al. | |
| 5,817,721 A | 10/1998 | Warzelhan et al. | |
| 5,823,988 A | 10/1998 | Orenga et al. | |
| 5,873,871 A * | 2/1999 | Lavash et al. | 604/386 |
| 5,900,322 A | 5/1999 | Buchanan et al. | |
| 5,916,678 A | 6/1999 | Jackson et al. | |
| 5,916,969 A | 6/1999 | Wang et al. | |

(Continued)

FOREIGN PATENT DOCUMENTS

DE 19802718 A1 7/1999
EP 0327505 A2 8/1989

(Continued)

OTHER PUBLICATIONS

Search Report and Written Opinion for PCT/IB2007/053959, Mar. 5, 2008.
ASTM D 1238 70 Measuring Flow Rates of Thermoplastics by Extrusion Plastometer, 1970.
ASTM D 1238 95 Flow Rates of Thermoplastics by Extrusion Plastometer, 1995.
ASTM D 3418 03 Transition Temperatures and Enthalpies of Fusion and Crystallization of Polymers by Differential Scanning Calorimetry, 2003.
ASTM 5034 95 Breaking Strenth and Elongation of Textile Fabrics (Grab Test), 1995.
ASTM D 5338 92 Determining Aerobic Biodegradation of Plastic Materials Under Controlled Composting Conditions, 1992.

*Primary Examiner* — Irina Krylova
(74) *Attorney, Agent, or Firm* — Dority & Manning, P.A.

(57) ABSTRACT

A film that is biodegradable and water-sensitive (e.g., water-soluble, water-dispersible, etc.) in that it loses its integrity over time in the presence of water is provided. More specifically, the film contains a combination of a biodegradable polyester and a water-sensitive thermoplastic starch. The desired water-sensitive attributes of film may be achieved in the present invention by selectively controlling a variety of aspects of the film construction, such as the nature of the components employed, the relative amount of each component, the manner in which the film is formed, and so forth.

10 Claims, 2 Drawing Sheets

(56) References Cited

U.S. PATENT DOCUMENTS

| | | |
|---|---|---|
| 5,932,497 A | 8/1999 | Morman et al. |
| 5,945,480 A | 8/1999 | Wang et al. |
| 5,948,710 A | 9/1999 | Pomplun et al. |
| 5,981,012 A | 11/1999 | Pomplun et al. |
| 5,985,396 A | 11/1999 | Kerins et al. |
| 5,997,981 A | 12/1999 | McCormack et al. |
| 6,011,092 A | 1/2000 | Seppälä et al. |
| 6,015,764 A | 1/2000 | McCormack et al. |
| 6,075,118 A | 6/2000 | Wang et al. |
| 6,096,809 A | 8/2000 | Lorcks et al. |
| 6,110,158 A * | 8/2000 | Kielpikowski ........... 604/385.28 |
| 6,111,163 A | 8/2000 | McCormack et al. |
| 6,160,199 A | 12/2000 | Noda |
| 6,214,907 B1 | 4/2001 | Tomka |
| 6,231,970 B1 | 5/2001 | Andersen et al. |
| 6,235,816 B1 * | 5/2001 | Lorcks et al. ................. 524/47 |
| 6,258,427 B1 | 7/2001 | Kerins et al. |
| 6,258,924 B1 | 7/2001 | Warzelhan et al. |
| 6,288,184 B1 | 9/2001 | Wilson, Jr. et al. |
| 6,294,238 B1 | 9/2001 | Pomplun et al. |
| 6,296,914 B1 | 10/2001 | Kerins et al. |
| 6,312,756 B1 | 11/2001 | Dudacek et al. |
| 6,348,524 B2 * | 2/2002 | Bastioli et al. ................. 524/47 |
| 6,380,445 B1 | 4/2002 | Rietz et al. |
| 6,387,528 B1 | 5/2002 | Pomplun et al. |
| 6,461,457 B1 | 10/2002 | Taylor et al. |
| 6,472,497 B2 | 10/2002 | Loercks et al. |
| 6,479,105 B2 | 11/2002 | Chang et al. |
| 6,489,533 B2 | 12/2002 | Imai et al. |
| 6,495,080 B1 | 12/2002 | Tsai et al. |
| 6,511,465 B1 | 1/2003 | Freiburger et al. |
| 6,514,602 B1 * | 2/2003 | Zhao et al. .................... 428/212 |
| 6,515,054 B1 | 2/2003 | Matsushita et al. |
| 6,530,910 B1 * | 3/2003 | Pomplun et al. .............. 604/364 |
| 6,531,642 B2 | 3/2003 | Kurata et al. |
| 6,534,610 B1 | 3/2003 | Wilson, Jr. et al. |
| 6,563,399 B2 | 5/2003 | Love |
| 6,564,399 B1 | 5/2003 | Teal |
| 6,569,137 B2 | 5/2003 | Suzuki et al. |
| 6,573,340 B1 | 6/2003 | Khemani et al. |
| 6,607,819 B2 | 8/2003 | Wang et al. |
| 6,616,787 B2 | 9/2003 | Imai et al. |
| 6,638,603 B1 | 10/2003 | Kerins et al. |
| 6,663,611 B2 | 12/2003 | Blaney et al. |
| 6,716,203 B2 | 4/2004 | Sorebo et al. |
| 6,747,186 B2 | 6/2004 | Shimizu |
| 6,783,826 B2 | 8/2004 | Sherrod et al. |
| 6,888,044 B2 | 5/2005 | Fell et al. |
| 6,890,872 B2 * | 5/2005 | Bond et al. ..................... 442/414 |
| 6,897,168 B2 | 5/2005 | Branham et al. |
| 6,908,966 B2 | 6/2005 | Chang et al. |
| 6,958,371 B1 | 10/2005 | Wang et al. |
| 6,960,371 B2 | 11/2005 | Bunyard et al. |
| 6,989,193 B2 | 1/2006 | Haile et al. |
| 6,994,865 B2 | 2/2006 | Branham et al. |
| 7,012,116 B1 | 3/2006 | Schertz et al. |
| 7,077,994 B2 | 7/2006 | Bond et al. |
| 7,094,817 B2 | 8/2006 | Halley et al. |
| 7,176,251 B1 * | 2/2007 | Bastioli et al. ................... 524/47 |
| 8,329,977 B2 * | 12/2012 | Wang et al. ..................... 604/364 |
| 2002/0028857 A1 | 3/2002 | Holy |
| 2002/0111596 A1 | 8/2002 | Fletcher et al. |
| 2002/0188041 A1 * | 12/2002 | Bond et al. ....................... 524/47 |
| 2003/0068951 A1 | 4/2003 | Boggs et al. |
| 2003/0108701 A1 * | 6/2003 | Bond et al. .................... 428/35.7 |
| 2003/0116462 A1 | 6/2003 | Sorebo et al. |
| 2003/0166748 A1 * | 9/2003 | Khemani et al. ................. 524/47 |
| 2004/0060112 A1 | 4/2004 | Fell et al. |
| 2004/0122135 A1 * | 6/2004 | Halley et al. .................... 524/47 |
| 2004/0122403 A1 | 6/2004 | Mitchler et al. |
| 2004/0225269 A1 * | 11/2004 | Zhao et al. ..................... 604/364 |
| 2004/0267217 A1 | 12/2004 | Dave et al. |
| 2005/0084634 A1 | 4/2005 | Giori |
| 2005/0113770 A1 | 5/2005 | Pedersen et al. |
| 2005/0182196 A1 * | 8/2005 | Khemani et al. ............... 525/178 |
| 2005/0245162 A1 | 11/2005 | McCormack et al. |
| 2005/0282008 A1 | 12/2005 | Haile et al. |
| 2005/0282456 A1 | 12/2005 | Zhao et al. |
| 2007/0241483 A1 | 10/2007 | Bastioli et al. |
| 2007/0264460 A1 * | 11/2007 | Del Tredici ..................... 428/43 |

FOREIGN PATENT DOCUMENTS

| | | |
|---|---|---|
| EP | 0417828 A1 | 3/1991 |
| EP | 0809680 B1 | 12/1997 |
| EP | 0947559 A2 | 10/1999 |
| EP | 0947559 A3 | 10/1999 |
| EP | 1116748 A1 | 7/2001 |
| JP | 09143893 A | 6/1997 |
| WO | WO 9202199 | 2/1992 |
| WO | WO 9620831 | 7/1996 |
| WO | WO 2005116118 A1 | 12/2005 |

* cited by examiner

US 8,592,641 B2

WATER-SENSITIVE BIODEGRADABLE FILM

BACKGROUND OF THE INVENTION

Films are employed in a wide variety of disposable goods, such as diapers, sanitary napkins, adult incontinence garments, bandages, etc. For example, many sanitary napkins have an adhesive strip on the backside of the napkin (the napkin surface opposite to the body-contacting surface) to affix the napkin to an undergarment and hold the napkin in place against the body. Before use, the adhesive strip is protected with a peelable release liner. Once removed, the peelable release liner must be discarded. Conventional release liners may contain a film or paper coated with a release coating. Such release-coated films or papers, however, do not readily disperse in water, and as such, disposal options are limited to depositing the release liner in a trash receptacle. Although disposing of conventional release liners in a toilet would be convenient to the consumer, it would potentially create blockages in the toilet.

In response to these and other problems, flushable release liners have been developed that are formed from a water-sensitive film. U.S. Pat. No. 6,296,914 to Kerins, et al. describes a water-sensitive film that may include, for instance, polyethylene oxide, ethylene oxide-propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triazinyl ethylene), or a combination thereof. Some of these polymers, however, are not thermoplastic and thus are not readily processed using thermoplastic film converting equipment. Further, these films are also not generally biodegradable and may thus further complicate the disposal process. Certain water-sensitive films also tend to lack good mechanical properties during use.

As such, a need currently exists for a film that exhibits good mechanical properties, and is also biodegradable and water-sensitive.

SUMMARY OF THE INVENTION

In accordance with one embodiment of the present invention, a water-sensitive biodegradable film is disclosed. The film comprises from about 1 wt. % to about 50 wt. % of at least one biodegradable polyester, wherein the biodegradable polyester has a melting point of from about 50° C. to about 180° C. and a glass transition temperature of about 25° C. or less. The film also comprises from about 50 wt. % to about 99 wt. % of at least one thermoplastic starch, wherein the water-sensitive thermoplastic starch includes from about 40 wt. % to about 95 wt. % of at least one starch and from about 5 wt. % to about 60 wt. % of at least one plasticizer. The film has a thickness of about 50 micrometers or less.

In accordance with another embodiment of the present invention, an absorbent article is disclosed that comprises a body portion that includes a liquid permeable topsheet, a generally liquid impermeable backsheet, and an absorbent core positioned between the backsheet and the topsheet. The absorbent article further comprises a release liner that defines a first surface and an opposing second surface, the first surface being disposed adjacent to an adhesive located on the absorbent article. The release liner, the backsheet, or both include a water-sensitive biodegradable film comprising at least one biodegradable polyester and at least one water-sensitive thermoplastic starch.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
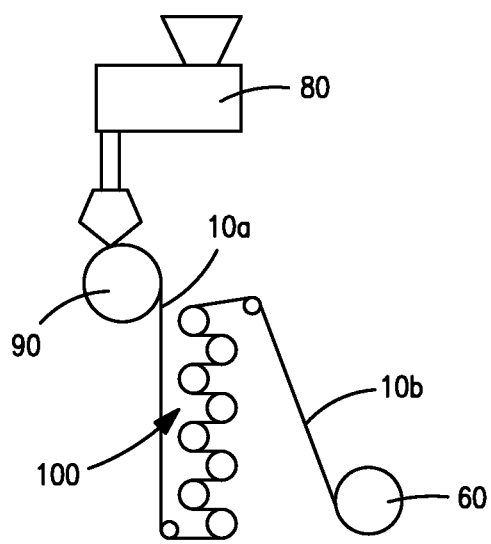
FIG. 1 is a schematic illustration of one embodiment of a method for forming a water-sensitive film in accordance with the present invention.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a film that is biodegradable and water-sensitive (e.g., water-soluble, water-dispersible, etc.) in that it loses its integrity over time in the presence of water. More specifically, the film contains a combination of a biodegradable polyester and a water-sensitive thermoplastic starch. The desired water-sensitive attributes of film may be achieved in the present invention by selectively controlling a variety of aspects of the film construction, such as the nature of the components employed, the relative amount of each component, the manner in which the film is formed, and so forth. In this regard, various embodiments of the present invention will now be described in more detail below.

I. Film Components

A. Biodegradable Polyester

The film of the present invention includes one or more biodegradable polyesters. The term "biodegradable" generally refers to a material that degrades from the action of naturally occurring microorganisms, such as bacteria, fungi, and algae; environmental heat; moisture; or other environmental factors, such as determined according to ASTM Test Method 5338.92. The biodegradable polyesters employed in the present invention typically have a relatively low glass transition temperature ("$T_g$") to reduce stiffness of the film and improve the processability of the polymers. For example, the $T_g$ may be about 25° C. or less, in some embodiments about 0° C. or less, and in some embodiments, about −10° C. or less. Likewise, the melting point of the biodegradable polyesters is also relatively low to improve the rate of biodegradation. For example, the melting point is typically from about 50° C. to about 180° C., in some embodiments from about 80° C. to about 160° C., and in some embodiments, from about 100° C. to about 140° C. The melting temperature and glass transition temperature may be determined using differential scanning calorimetry ("DSC") in accordance with ASTM D-3417 as is well known in the art. Such tests may be employed using a THERMAL ANALYST 2910 Differential Scanning Calorimeter (outfitted with a liquid nitrogen cooling accessory) and with a THERMAL ANALYST 2200 (version 8.10) analysis software program, which are available from T.A. Instruments Inc. of New Castle, Del.

The biodegradable polyesters employed in the film of the present invention may also have a number average molecular weight ("$M_n$") ranging from about 40,000 to about 120,000 grams per mole, in some embodiments from about 50,000 to about 100,000 grams per mole, and in some embodiments, from about 60,000 to about 85,000 grams per mole. Likewise, the polyesters may also have a weight average molecular weight ("$M_w$") ranging from about 70,000 to about 240,000 grams per mole, in some embodiments from about 80,000 to about 190,000 grams per mole, and in some embodiments, from about 100,000 to about 150,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 4.0, in some embodiments from about 1.2 to about 3.0, and in some embodiments, from about 1.4 to about 2.0. The weight and number average molecular weights may be determined by methods known to those skilled in the art.

The biodegradable polyesters may also have an apparent viscosity of from about 100 to about 1000 Pascal seconds (Pa·s), in some embodiments from about 200 to about 800 Pa·s, and in some embodiments, from about 300 to about 600 Pa·s, as determined at a temperature of 170° C. and a shear rate of 1000 sec$^{-1}$. The melt flow index of the biodegradable polyesters may also range from about 0.1 to about 10 grams per 10 minutes, in some embodiments from about 0.5 to about 8 grams per 10 minutes, and in some embodiments, from about 1 to about 5 grams per 10 minutes. The melt flow index is the weight of a polymer (in grams) that may be forced through an extrusion rheometer orifice (0.0825-inch diameter) when subjected to a load of 2160 grams in 10 minutes at a certain temperature (e.g., 190° C.), measured in accordance with ASTM Test Method D1238-E.

Of course, the melt flow index of the biodegradable polyesters will ultimately depend upon the selected film-forming process. For example, when extruded as a cast film, higher melt flow index polymers are typically desired, such as about 4 grams per 10 minutes or more, in some embodiments from about 5 to about 12 grams per 10 minutes, and in some embodiments, from about 7 to about 9 grams per 10 minutes. Likewise, when formed as a blown film, lower melt flow index polymers are typically desired, such as less than about 12 grams per 10 minutes or less, in some embodiments from about 1 to about 7 grams per 10 minutes, and in some embodiments, from about 2 to about 5 grams per 10 minutes.

Examples of suitable biodegradable polyesters include aliphatic polyesters, such as polycaprolactone, polyesteramides, modified polyethylene terephthalate, polylactic acid (PLA) and its copolymers, terpolymers based on polylactic acid, polyglycolic acid, polyalkylene carbonates (such as polyethylene carbonate), polyhydroxyalkanoates (PHA), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.); aromatic polyesters and modified aromatic polyesters; and aliphatic-aromatic copolyesters. In one particular embodiment, the biodegradable polyester is an aliphatic-aromatic copolyester (e.g., block, random, graft, etc.). The aliphatic-aromatic copolyester may be synthesized using any known technique, such as through the condensation polymerization of a polyol in conjunction with aliphatic and aromatic dicarboxylic acids or anhydrides thereof. The polyols may be substituted or unsubstituted, linear or branched, polyols selected from polyols containing 2 to about 12 carbon atoms and polyalkylene ether glycols containing 2 to 8 carbon atoms. Examples of polyols that may be used include, but are not limited to, ethylene glycol, diethylene glycol, propylene glycol, 1,2-propanediol, 1,3-propanediol, 2,2-dimethyl-1,3-propanediol, 1,2-butanediol, 1,3-butanediol, 1,4-butanediol, 1,2-pentanediol, 1,5-pentanediol, 1,6-hexanediol, polyethylene glycol, diethylene glycol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, cyclopentanediol, triethylene glycol, and tetraethylene glycol. Preferred polyols include 1,4-butanediol; 1,3-propanediol; ethylene glycol; 1,6-hexanediol; diethylene glycol; and 1,4-cyclohexanedimethanol.

Representative aliphatic dicarboxylic acids that may be used include substituted or unsubstituted, linear or branched, non-aromatic dicarboxylic acids selected from aliphatic dicarboxylic acids containing 1 to about 10 carbon atoms, and derivatives thereof. Non-limiting examples of aliphatic dicarboxylic acids include malonic, malic, succinic, oxalic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, and 2,5-norbornanedicarboxylic. Representative aromatic dicarboxylic acids that may be used include substituted and unsubstituted, linear or branched, aromatic dicarboxylic acids selected from aromatic dicarboxylic acids containing 1 to about 6 carbon atoms, and derivatives thereof. Non-limiting examples of aromatic dicarboxylic acids include terephthalic acid, dimethyl terephthalate, isophthalic acid, dimethyl isophthalate, 2,6-napthalene dicarboxylic acid, dimethyl-2,6-naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4,4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), etc., and mixtures thereof.

The polymerization may be catalyzed by a catalyst, such as a titanium-based catalyst (e.g., tetraisopropyltitanate, tetraisopropoxy titanium, dibutoxydiacetoacetoxy titanium, or tetrabutyltitanate). If desired, a diisocyanate chain extender may be reacted with the copolyester to increase its molecular weight. Representative diisocyanates may include toluene 2,4-diisocyanate, toluene 2,6-diisocyanate, 2,4'-diphenylmethane diisocyanate, naphthylene-1,5-diisocyanate, xylylene diisocyanate, hexamethylene diisocyanate ("HMDI"), isophorone diisocyanate and methylenebis(2-isocyanatocyclohexane). Trifunctional isocyanate compounds may also be employed that contain isocyanurate and/or biurea groups with a functionality of not less than three, or to replace the diisocyanate compounds partially by tri-or polyisocyanates. The preferred diisocyanate is hexamethylene diisocyanate. The amount of the chain extender employed is typically from about 0.3 to about 3.5 wt. %, in some embodiments, from about 0.5 to about 2.5 wt. % based on the total weight percent of the polymer.

The copolyesters may either be a linear polymer or a long-chain branched polymer. Long-chain branched polymers are generally prepared by using a low molecular weight branching agent, such as a polyol, polycarboxylic acid, hydroxy acid, and so forth. Representative low molecular weight polyols that may be employed as branching agents include glycerol, trimethylolpropane, trimethylolethane, polyethertriols, 1,2,4-butanetriol, pentaerythritol, 1,2,6-hexanetriol, sorbitol, 1,1,4,4,-tetrakis (hydroxymethyl) cyclohexane, tris(2-hydroxyethyl) isocyanurate, and dipentaerythritol. Representative higher molecular weight polyols (molecular weight of 400 to 3000) that may be used as branching agents include triols derived by condensing alkylene oxides having 2 to 3 carbons, such as ethylene oxide and propylene oxide with polyol initiators. Representative polycarboxylic acids that may be used as branching agents include hemimellitic acid, trimellitic (1,2,4-benzenetricarboxylic) acid and anhydride, trimesic (1,3,5-benzenetricarboxylic) acid, pyromellitic acid and anhydride, benzenetetracarboxylic acid, benzophenone tetracarboxylic acid, 1,1,2,2-ethane-tetracarboxylic acid, 1,1, 2-ethanetricarboxylic acid, 1,3,5-pentanetricarboxylic acid, and 1,2,3,4-cyclopentanetetracarboxylic acid. Representative hydroxy acids that may be used as branching agents include malic acid, citric acid, tartaric acid, 3-hydroxyglutaric acid, mucic acid, trihydroxyglutaric acid, 4-carboxyphthalic anhydride, hydroxyisophthalic acid, and 4-(beta-hydroxyethyl)phthalic acid. Such hydroxy acids contain a combination of 3 or more hydroxyl and carboxyl groups. Especially preferred branching agents include trimellitic acid, trimesic acid, pentaerythritol, trimethylol propane and 1,2,4-butanetriol.

The aromatic dicarboxylic acid monomer constituent may be present in the copolyester in an amount of from about 10 mole % to about 40 mole %, in some embodiments from about 15 mole % to about 35 mole %, and in some embodiments, from about 15 mole % to about 30 mole %. The aliphatic dicarboxylic acid monomer constituent may likewise be present in the copolyester in an amount of from about 15 mole % to about 45 mole %, in some embodiments from about 20 mole % to about 40 mole %, and in some embodiments, from about 25 mole % to about 35 mole %. The polyol monomer constituent may also be present in the aliphatic-aromatic copolyester in an amount of from about 30 mole % to about 65 mole %, in some embodiments from about 40 mole % to about 50 mole %, and in some embodiments, from about 45 mole % to about 55 mole %.

In one particular embodiment, for example, the aliphatic-aromatic copolyester may comprise the following structure:

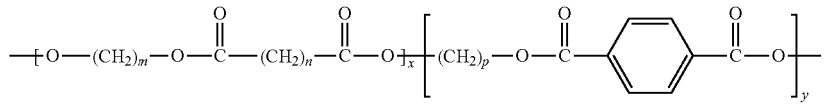

wherein, m is an integer from 2 to 10, in some embodiments from 2 to 4, and in one embodiment, 4;

n is an integer from 0 to 18, in some embodiments from 2 to 4, and in one embodiment, 4;

p is an integer from 2 to 10, in some embodiments from 2 to 4, and in one embodiment, 4;

x is an integer greater than 1; and y is an integer greater than 1. One example of such a copolyester is polybutylene adipate terephthalate, which is commercially available under the designation ECOFLEX® F BX 7011 from BASF Corp. Another example of a suitable copolyester containing an aromatic terephtalic acid monomer constituent is available under the designation ENPOL™ 8060M from IRE Chemicals (South Korea). Other suitable aliphatic-aromatic copolyesters may be described in U.S. Pat. Nos. 5,292,783; 5,446,079; 5,559,171; 5,580,911; 5,599,858; 5,817,721; 5,900,322; and 6,258,924, which are incorporated herein in their entirety by reference thereto for all purposes.

B. Thermoplastic Starch

A thermoplastic starch is employed in the film of the present invention that is water-sensitive in that it contains one or more starches that are generally dispersible in water. Starch is a natural polymer composed of amylose and amylopectin. Amylose is essentially a linear polymer having a molecular weight in the range of 100,000-500,000, whereas amylopectin is a highly branched polymer having a molecular weight of up to several million. Although starch is produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm.

Broadly speaking, any natural (unmodified) and/or modified starch having the desired water sensitivity properties may be employed in the present invention. Modified starches, for instance, are often employed that have been chemically modified by typical processes known in the art (e.g., esterification, etherification, oxidation, acid hydrolysis, enzymatic hydrolysis, etc.). Starch ethers and/or esters may be particularly desirable, such as hydroxyalkyl starches, carboxymethyl starches, etc. The hydroxyalkyl group of hydroxylalkyl starches may contain, for instance, 1 to 10 carbon atoms, in some embodiments from 1 to 6 carbon atoms, in some embodiments from 1 to 4 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch.

A plasticizer is also typically employed in the thermoplastic starch to render the starch melt-processible. Starches normally exist in the form of granules that have a coating or outer membrane that encapsulates the more water-soluble amylose and amylopectin chains within the interior of the granule. When heated, polar solvents ("plasticizers") may soften and penetrate the outer membrane and cause the inner starch chains to absorb water and swell. This swelling will, at some point, cause the outer shell to rupture and result in an irreversible destructurization of the starch granule. Once destructurized, the starch polymer chains containing amylose and amylopectin polymers, which are initially compressed within the granules, will stretch out and form a generally disordered intermingling of polymer chains. Upon resolidification, however, the chains may reorient themselves to form crystalline or amorphous solids having varying strengths depending on the orientation of the starch polymer chains. Because the starch (natural or modified) is thus capable of melting and resolidifying, it is generally considered a "thermoplastic starch."

Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, glycerol, and sorbitol), polyols (e.g., ethylene glycol, propylene glycol, dipropylene glycol, butylene glycol, and hexane triol), etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids may also be used, such as ethylene acrylic acid, ethylene maleic acid, butadiene acrylic acid, butadiene maleic acid, propylene acrylic acid, propylene maleic acid, and other hydrocarbon based acids. A low molecular weight plasticizer is preferred, such as less than about 20,000 g/mol, preferably less than about 5,000 g/mol and more preferably less than about 1,000 g/mol.

The relative amount of starches and plasticizers employed in the thermoplastic starch may vary depending on a variety of factors, such as the molecular weight of the starch, the type of starch (e.g., modified or unmodified), the affinity of the plasticizer for the starch, etc. Typically, however, starches constitute from about 40 wt. % to about 95 wt. %, in some embodiments from about 50 wt. % to about 90 wt. %, and in some embodiments, from about 60 wt. % to about 80 wt. % of the thermoplastic composition. Likewise, plasticizers typically constitute from about 5 wt. % to about 60 wt. %, in some embodiments from about 10 wt. % to about 50 wt. %, and in some embodiments, from about 20 wt. % to about 40 wt. % of the thermoplastic composition. It should be understood that the weight of starch referenced herein includes any bound water that naturally occurs in the starch before mixing it with other components to form the thermoplastic starch. Starches, for instance, typically have a bound water content of about 5% to 16% by weight of the starch.

Other additives may also be employed in the thermoplastic starch to facilitate its use in the film of the present invention. Dispersion aids, for instance, may be employed to help create a uniform dispersion of the starch/plasticizer mixture and retard or prevent separation of the thermoplastic starch into constituent phases. Likewise, the dispersion aids may also improve the water dispersibility of the film. When employed, the dispersion aid(s) typically constitute from about 0.01 wt. % to about 10 wt. %, in some embodiments from about 0.1 wt. % to about 5 wt. %, and in some embodiments, from about 0.5 wt. % to about 4 wt. % of the thermoplastic composition.

Although any dispersion aid may generally be employed in the present invention, surfactants having a certain hydrophilic/lipophilic balance ("HLB") may improve the long-term stability of the composition. The HLB index is well known in the art and is a scale that measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. In some embodiments of the present invention, the HLB value of the surfactants is from about 1 to about 20, in some embodiments from about 1 to about 15 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain contaiing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

The thermoplastic starch may be formed using any of a variety of known techniques. For example, in one embodiment, the thermoplastic starch is formed prior to being combined with the biodegradable polyester. In such embodiments, the starch may be initially blended with the plasticizer, emulsifying surfactant, etc., to form the thermoplastic starch. Batch and/or continuous melt blending techniques may be employed. For example, a mixer/kneader, Banbury mixer, Farrel continuous mixer, single-screw extruder, twin-screw extruder, roll mill, etc., may be utilized to blend the materials. One particularly suitable melt-blending device is a co-rotating, twin-screw extruder (e.g., USALAB twin-screw extruder available from Thermo Electron Corporation of Stone, England or an extruder available from Werner-Pfreiderer from Ramsey, N.J.). Such extruders may include feeding and venting ports and provide high intensity distributive and dispersive mixing. For example, a starch composition may be initially fed to a feeding port of the twin-screw extruder. Thereafter, the plasticizer may be injected into the starch composition. Alternatively, the starch composition may be simultaneously fed to the feed throat of the extruder or separately at a different point along its length. Melt blending may occur at any of a variety of temperatures, such as from about 30° C. to about 200° C., in some embodiments, from about 40° C. to about 160° C., and in some embodiments, from about 50° C. to about 150° C.

Regardless of the manner in which it is formed, the amount of the thermoplastic starch employed in the film is controlled in the present invention to achieve a desirable balance between biodegradability, mechanical strength, and water-sensitivity. That is, the mechanical properties and biodegradability of the film is generally improved with increasing amounts of biodegradable polyesters. However, if too much of the biodegradable polyester is employed, the film may not achieve the desired water sensitivity. Thus, thermoplastic starches (natural or modified) typically constitute from about 50 wt. % to about 99 wt. %, in some embodiments from about 55 wt. % to about 98 wt. %, and in some embodiments, from about 60 wt. % to about 95 wt. % of the film. Likewise, biodegradable polyesters typically constitute from about 1 wt. % to about 50 wt. %, in some embodiments from about 2 wt. % to about 45 wt. %, and in some embodiments, from about 5 wt. % to about 40 wt. % of the film.

C. Other Components

In addition to the components noted above, other additives may also be incorporated into the film of the present invention, such as melt stabilizers, processing stabilizers, heat stabilizers, light stabilizers, antioxidants, heat aging stabilizers, whitening agents, antiblocking agents, bonding agents, lubricants, fillers, etc. Fillers, for example, are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman, et al.; U.S. Pat. No. 6,461,457 to Taylor, et al., which are incorporated herein in their entirety by reference thereto for all purposes. Further, hindered phenols are commonly used as an antioxidant in the production of films. Some suitable hindered phenols include those available from Ciba Specialty Chemicals under the trade name "Irganox®", such as Irganox® 1076, 1010, or E 201. Moreover, bonding agents may also be added to the film to facilitate bonding of the film to additional materials (e.g., nonwoven webs). Examples of such bonding agents include hydrogenated hydrocarbon resins. Other suitable bonding agents are described in U.S. Pat. No. 4,789,699 to Kieffer et al. and U.S. Pat. No. 5,695,868 to McCormack, which are incorporated herein in their entirety by reference thereto for all purposes.

II. Film Construction

The film of the present invention may be mono- or multilayered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers, wherein the base layer is formed from a blend of the biodegradable polyester and thermoplastic starch. In most embodiments, the skin layer(s) are formed from a biodegradable polyester and/or thermoplastic starch, such as described above. It should be understood, however, that other polymers may also be employed in the skin layer(s), such as polyolefin polymers (e.g., linear low-density polyethylene (LLDPE) or polypropylene). The term "linear low density polyethylene" refers to polymers of ethylene and higher alpha olefin comonomers, such as $C_3$-$C_{12}$ and combinations thereof, having a Melt Index (as measured by ASTM D-1238) of from about 0.5 to about 30 grams per 10 minutes at 190° C. Examples of predominately linear polyolefin polymers include, without limitation, polymers produced from the following monomers: ethylene, propylene, 1-butene, 4-methylpentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers. Additional film-forming polymers that may be suitable for use with the present invention, alone or in combination with other polymers, include ethylene vinyl acetate, ethylene ethyl acrylate, ethylene acrylic acid, ethylene methyl acrylate, ethylene normal butyl acrylate, nylon, ethylene vinyl alcohol, polystyrene, polyurethane, and so forth.

Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs. et al., all of which are incorporated herein in their entirety by reference thereto for all purposes. In yet another embodiment, however, the film is formed using a casting technique.

Referring to FIG. 1, for instance, one embodiment of a method for forming a cast film is shown. The raw materials (e.g., biodegradable polyester, thermoplastic starch, etc.) may be supplied to a melt blending device, either separately or as a blend. In one embodiment, for example, a pre-formed thermoplastic starch and biodegradable polyester are separately supplied to a melt blending device where they are dispersively blended in a manner such as described above. For example, an extruder may be employed that includes feeding and venting ports. In one embodiment, the biodegradable polyester may be fed to a feeding port of the twin-screw extruder and melted. Thereafter, the thermoplastic starch may be fed into the polymer melt. Regardless, the materials are blended under high shear/pressure and heat to ensure sufficient mixing. For example, melt blending may occur at a temperature of from about 50° C. to about 300° C., in some embodiments, from about 70° C. to about 250° C., and in some embodiments, from about 90° C. to about 180° C. Likewise, the apparent shear rate during melt blending may range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows.

Thereafter, the extruded material may be immediately chilled and cut into pellet form. In the particular embodiment of FIG. 1, the compounded material (not shown) is then supplied to an extrusion apparatus 80 and cast onto a casting roll 90 to form a single-layered precursor film 10a. If a multilayered film is to be produced, the multiple layers are coextruded together onto the casting roll 90. The casting roll 90 may optionally be provided with embossing elements to impart a pattern to the film. Typically, the casting roll 90 is kept at temperature sufficient to solidify and quench the sheet 10a as it is formed, such as from about 20 to 60° C. If desired, a vacuum box may be positioned adjacent to the casting roll 90 to help keep the precursor film 10a close to the surface of the roll 90. Additionally, air knives or electrostatic pinners may help force the precursor film 10a against the surface of the casting roll 90 as it moves around a spinning roll. An air knife is a device known in the art that focuses a stream of air at a very high flow rate to pin the edges of the film.

Once cast, the film 10a may then be optionally oriented in one or more directions to further improve film uniformity and reduce thickness. Orientation may also form micropores in a film containing a filler, thus providing breathability to the film. For example, the film may be immediately reheated to a temperature below the melting point of one or more polymers in the film, but high enough to enable the composition to be drawn or stretched. In the case of sequential orientation, the "softened" film is drawn by rolls rotating at different speeds of rotation such that the sheet is stretched to the desired draw ratio in the longitudinal direction (machine direction). This "uniaxially" oriented film may then be laminated to a fibrous web. In addition, the uniaxially oriented film may also be oriented in the cross-machine direction to form a "biaxially oriented" film. For example, the film may be clamped at its lateral edges by chain clips and conveyed into a tenter oven. In the tenter oven, the film may be reheated and drawn in the cross-machine direction to the desired draw ratio by chain clips diverged in their forward travel.

Referring again to FIG. 1, for instance, one method for forming a uniaxially oriented film is shown. As illustrated, the precursor film 10a is directed to a film-orientation unit 100 or machine direction orienter ("MDO"), such as commercially available from Marshall and Willams, Co. of Providence, R.I. The MDO has a plurality of stretching rolls (such as from 5 to 8) which progressively stretch and thin the film in the machine direction, which is the direction of travel of the film through the process as shown in FIG. 1. While the MDO 100 is illustrated with eight rolls, it should be understood that the number of rolls may be higher or lower, depending on the level of stretch that is desired and the degrees of stretching between each roll. The film may be stretched in either single or multiple discrete stretching operations. It should be noted that some of the rolls in an MDO apparatus may not be operating at progressively higher speeds. If desired, some of the rolls of the MDO 100 may act as preheat rolls. If present, these first few rolls heat the film 10a above room temperature (e.g., to 125° F.). The progressively faster speeds of adjacent rolls in the MDO act to stretch the film 10a. The rate at which the stretch rolls rotate determines the amount of stretch in the film and final film weight.

The resulting film 10b may then be wound and stored on a take-up roll 60. While not shown here, various additional potential processing and/or finishing steps known in the art, such as slitting, treating, aperturing, printing graphics, or lamination of the film with other layers (e.g., nonwoven web materials), may be performed without departing from the spirit and scope of the invention.

The thickness of the resulting water-sensitive biodegradable film may generally vary depending upon the desired use. Nevertheless, the film thickness is typically minimized to reduce the time needed for the film to disperse in water. Thus, in most embodiments of the present invention, the water-sensitive biodegradable film has a thickness of about 50 micrometers or less, in some embodiments from about 1 to about 40 micrometers, in some embodiments from about 2 to about 35 micrometers, and in some embodiments, from about 5 to about 30 micrometers.

Despite having such a small thickness and good sensitivity in water, the film of the present invention is nevertheless able to retain good dry mechanical properties during use. One parameter that is indicative of the relative dry strength of the film is the ultimate tensile strength, which is equal to the peak stress obtained in a stress-strain curve. Desirably, the film of the present invention exhibits an ultimate tensile strength in the machine direction ("MD") of from about 10 to about 80 Megapascals (MPa), in some embodiments from about 15 to about 60 MPa, and in some embodiments, from about 20 to about 50 MPa, and an ultimate tensile strength in the cross-machine direction ("CD") of from about 2 to about 40 Megapascals (MPa), in some embodiments from about 4 to about 40 MPa, and in some embodiments, from about 5 to about 30 MPa. Although possessing good strength, it is also desirable that the film is not too stiff. One parameter that is indicative of the relative stiffness of the film (when dry) is Young's modulus of elasticity, which is equal to the ratio of the tensile stress to the tensile strain and is determined from the slope of a stress-strain curve. For example, the film typically exhibits a Young's modulus in the machine direction ("MD") of from about 50 to about 1200 Megapascals ("MPa"), in some embodiments from about 200 to about 1000 MPa, and in some embodiments, from about 400 to about 800 MPa, and a Young's modulus in the cross-machine direction ("CD") of from about 50 to about 1000 Megapascals ("MPa"), in some embodiments from about 100 to about 800 MPa, and in some embodiments, from about 150 to about 500 MPa.

The water-sensitive biodegradable film of the present invention may be used in a wide variety of applications. For example, as indicated above, the film may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins, pantiliners, etc.), swim wear, baby wipes, and so forth; medical absorbent articles, such as garments, fenestration materials, underpads, bedpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., all of which are incorporated herein in their entirety by reference thereto for all purposes. Materials and processes suitable for forming such absorbent articles are well known to those skilled in the art.

As is well known in the art, the absorbent article may be provided with adhesives (e.g., pressure-sensitive adhesives) that help removably secure the article to the crotch portion of an undergarment and/or wrap up the article for disposal. Suitable pressure-sensitive adhesives, for instance, may include acrylic adhesives, natural rubber adhesives, tackified block copolymer adhesives, polyvinyl acetate adhesives, ethylene vinyl acetate adhesives, silicone adhesives, polyurethane adhesives, thermosettable pressure-sensitive adhesives, such as epoxy acrylate or epoxy polyester pressure-sensitive adhesives, etc. Such pressure-sensitive adhesives are known in the art and are described in the Handbook of Pressure Sensitive Adhesive Technology, Satas (Donatas), 1989, $2^{nd}$ edition, Van Nostrand Reinhold. The pressure sensitive adhesives may also include additives such as cross-linking agents, fillers, gases, blowing agents, glass or polymeric microspheres, silica, calcium carbonate fibers, surfactants, and so forth. The additives are included in amounts sufficient to affect the desired properties.

The location of the adhesive on the absorbent article is not critical and may vary widely depending on the intended use of the article. For example, certain feminine hygiene products (e.g., sanitary napkins) may have wings or flaps that laterally from a central absorbent core and are intended to be folded around the edges of the wearer's panties in the crotch region. The flaps may be provided with an adhesive (e.g., pressure-sensitive adhesive) for affixing the flaps to the underside of the wearer's panties.

Regardless of the particular location of the adhesive, however, a release liner may be employed to cover the adhesive, thereby protecting it from dirt, drying out, and premature sticking prior to use. The release liner may contain a release coating that enhances the ability of the liner to be peeled from an adhesive. The release coating contains a release agent, such as a hydrophobic polymer. Exemplary hydrophobic polymers include, for instance, silicones (e.g., polysiloxanes, epoxy silicones, etc.), perfluoroethers, fluorocarbons, polyurethanes, and so forth. Examples of such release agents are described, for instance, in U.S. Pat. No. 6,530,910 to Pomplun, et al.; U.S. Pat. No. 5,985,396 to Kerins, et al.; and U.S. Pat. No. 5,981,012 to Pomplun, et al., which are incorporated herein in their entirety by reference thereto for all purposes. One particularly suitable release agent is an amorphous polyolefin having a melt viscosity of about 400 to about 10,000 cps at 190° C., such as made by the U.S. Rexene Company under the tradename REXTAC® (e.g., RT2315, RT2535 and RT2330). The release coating may also contain a detackifier, such as a low molecular weight, highly branched polyolefin. A particularly suitable low molecular weight, highly branched polyolefin is VYBAR® 253, which is made by the Petrolite Corporation. Other additives may also be employed in the release coating, such as compatibilizers, processing aids, plasticizers, tackifiers, slip agents, and antimicrobial agents, and so forth. The release coating may be applied to one or both surfaces of the liner, and may cover all or only a portion of a surface. Any suitable technique may be employed to apply the release coating, such as solvent-based coating, hot melt coating, solventless coating, etc. Solvent-based coatings are typically applied to the release liner by processes such as roll coating, knife coating, curtain coating, gravure coating, wound rod coating, and so forth. The solvent (e.g., water) is then removed by drying in an oven, and the coating is optionally cured in the oven. Solventless coatings may include solid compositions, such as silicones or epoxy silicones, which are coated onto the liner and then cured by exposure to ultraviolet light. Optional steps include priming the liner before coating or surface modification of the liner, such as with corona treatment. Hot melt coatings, such as polyethylenes or perfluoroethers, may be heated and then applied through a die or with a heated knife. Hot melt coatings may be applied by co-extruding the release agent with the release liner in blown film or sheet extruder for ease of coating and for process efficiency.

Figure 2:
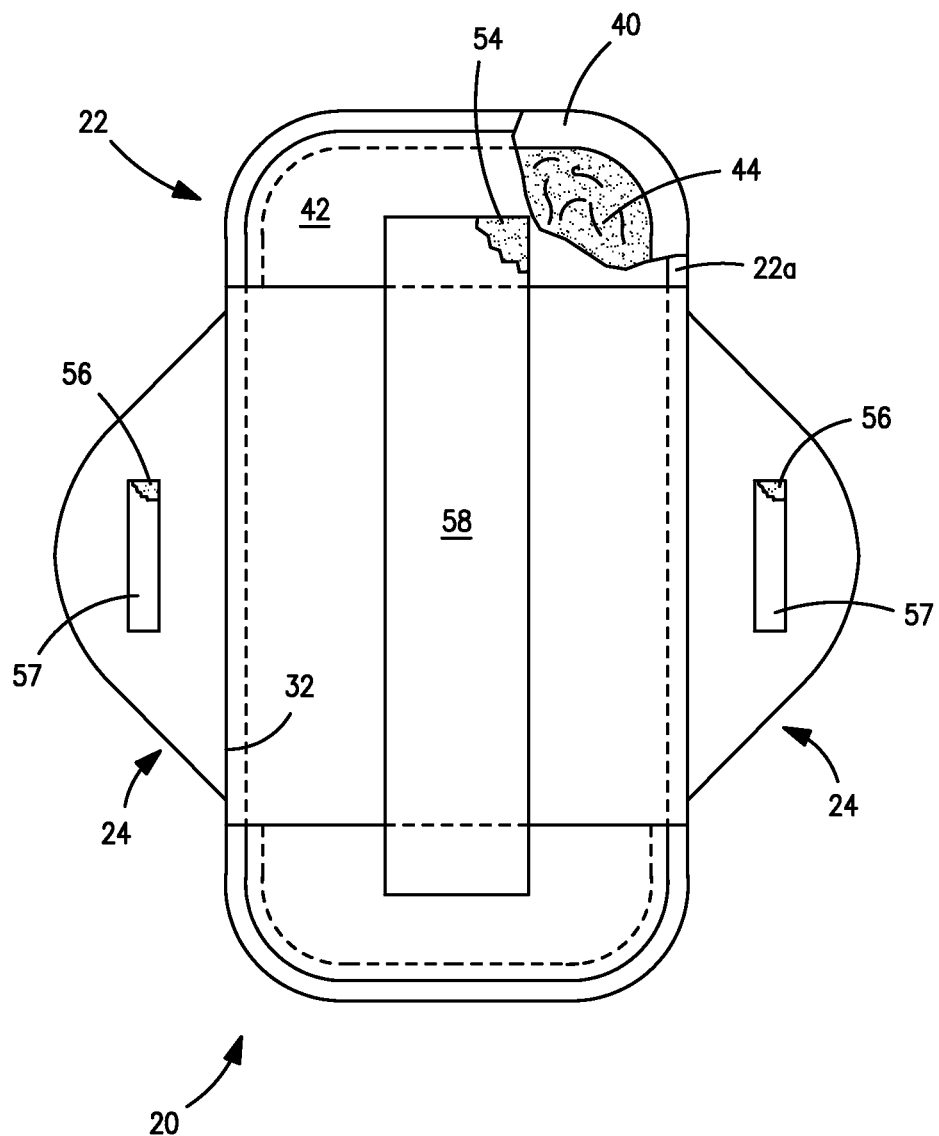
FIG. 2 is a top view of an absorbent article that may be formed in accordance with one embodiment of the present invention.

To facilitate its ability to be easily disposed, the release liner may be formed from a water-sensitive biodegradable film in accordance with the present invention. In this regard, one particular embodiment of a sanitary napkin that may employ the water-sensitive biodegradable film of the present invention will now be described in more detail. For purposes of illustration only, an absorbent article 20 is shown in FIG. 2 as a sanitary napkin for feminine hygiene. In the illustrated embodiment, the absorbent article 20 includes a main body portion 22 containing a topsheet 40, an outer cover or backsheet 42, an absorbent core 44 positioned between the backsheet 42 and the topsheet 40, and a pair of flaps 24 extending from each longitudinal side 22*a* of the main body portion 22. The topsheet 40 defines a bodyfacing surface of the absorbent article 20. The absorbent core 44 is positioned inward from the outer periphery of the absorbent article 20 and includes a body-facing side positioned adjacent the topsheet 40 and a garment-facing surface positioned adjacent the backsheet 42.

The topsheet 40 is generally designed to contact the body of the user and is liquid-permeable. The topsheet 40 may surround the absorbent core 44 so that it completely encases the absorbent article 20. Alternatively, the topsheet 40 and the backsheet 42 may extend beyond the absorbent core 44 and be peripherally joined together, either entirely or partially, using known techniques. Typically, the topsheet 40 and the backsheet 42 are joined by adhesive bonding, ultrasonic bonding, or any other suitable joining method known in the art. The topsheet 40 is sanitary, clean in appearance, and somewhat opaque to hide bodily discharges collected in and absorbed by the absorbent core 44. The topsheet 40 further exhibits good strike-through and rewet characteristics permitting bodily discharges to rapidly penetrate through the topsheet 40 to the absorbent core 44, but not allow the body fluid to flow back through the topsheet 40 to the skin of the wearer. For example, some suitable materials that may be used for the topsheet 40 include nonwoven materials, perforated thermoplastic films, or combinations thereof. A nonwoven fabric made from polyester, polyethylene, polypropylene, bicomponent, nylon, rayon, or like fibers may be utilized. For instance, a white uniform spunbond material is particularly desirable because the color exhibits good masking properties to hide menses that has passed through it. U.S. Pat. No. 4,801,494 to Datta, et al. and U.S. Pat. No. 4,908,026 to Sukiennik, et al. teach various other cover materials that may be used in the present invention.

The topsheet 40 may also contain a plurality of apertures (not shown) formed therethrough to permit body fluid to pass more readily into the absorbent core 44. The apertures may be randomly or uniformly arranged throughout the topsheet 40, or they may be located only in the narrow longitudinal band or strip arranged along the longitudinal axis X-X of the absorbent article 20. The apertures permit rapid penetration of body fluid down into the absorbent core 44. The size, shape, diameter and number of apertures may be varied to suit one's particular needs.

As stated above, the absorbent article also includes a backsheet 42. The backsheet 42 is generally liquid-impermeable and designed to face the inner surface, i.e., the crotch portion of an undergarment (not shown). The backsheet 42 may permit a passage of air or vapor out of the absorbent article 20, while still blocking the passage of liquids. Any liquid-impermeable material may generally be utilized to form the backsheet 42. For example, one suitable material that may be utilized is a microembossed polymeric film, such as polyethylene or polypropylene. In particular embodiments, a polyethylene film is utilized that has a thickness in the range of about. 0.2 mils to about 5.0 mils, and particularly between about 0.5 to about 3.0 mils.

The absorbent article 20 also contains an absorbent core 44 positioned between the topsheet 40 and the backsheet 42. The absorbent core 44 may be formed from a single absorbent member or a composite containing separate and distinct absorbent members. It should be understood, however, that any number of absorbent members may be utilized in the present invention. For example, in one embodiment, the absorbent core 44 may contain an intake member (not shown) positioned between the topsheet 40 and a transfer delay member (not shown). The intake member may be made of a material that is capable of rapidly transferring, in the z-direction, body fluid that is delivered to the topsheet 40. The intake member may generally have any shape and/or size desired. In one embodiment, the intake member has a rectangular shape, with a length equal to or less than the overall length of the absorbent article 20, and a width less than the width of the absorbent article 20. For example, a length of between about 150 mm to about 300 mm and a width of between about 10 mm to about 60 mm may be utilized.

Any of a variety of different materials may be used for the intake member to accomplish the above-mentioned functions. The material may be synthetic, cellulosic, or a combination of synthetic and cellulosic materials. For example, airlaid cellulosic tissues may be suitable for use in the intake member. The airlaid cellulosic tissue may have a basis weight ranging from about 10 grams per square meter (gsm) to about 300 gsm, and in some embodiments, between about 100 gsm to about 250 gsm. In one embodiment, the airlaid cellulosic tissue has a basis weight of about 200 gsm. The airlaid tissue may be formed from hardwood and/or softwood fibers. The airlaid tissue has a fine pore structure and provides an excellent wicking capacity, especially for menses.

If desired, a transfer delay member (not shown) may be positioned vertically below the intake member. The transfer delay member may contain a material that is less hydrophilic than the other absorbent members, and may generally be characterized as being substantially hydrophobic. For example, the transfer delay member may be a nonwoven fibrous web composed of a relatively hydrophobic material, such as polypropylene, polyethylene, polyester or the like, and also may be composed of a blend of such materials. One example of a material suitable for the transfer delay member is a spunbond web composed of polypropylene, multi-lobal fibers. Further examples of suitable transfer delay member materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay member are described in U.S. Pat. No. 4,798,603 to Meyer, et al. and U.S. Pat. No. 5,248,309 to Serbiak, et al., which are incorporated herein in their entirety by reference thereto for all purposes. To adjust the performance of the invention, the transfer delay member may also be treated with a selected amount of surfactant to increase its initial wettability.

The transfer delay member may generally have any size, such as a length of about 150 mm to about 300 mm. Typically, the length of the transfer delay member is approximately equal to the length of the absorbent article 20. The transfer delay member may also be equal in width to the intake member, but is typically wider. For example, the width of the transfer delay member may be from between about 50 mm to about 75 mm, and particularly about 48 mm. The transfer delay member typically has a basis weight less than that of the other absorbent members. For example, the basis weight of the transfer delay member is typically less than about 150 grams per square meter (gsm), and in some embodiments, between about 10 gsm to about 100 gsm. In one particular embodiment, the transfer delay member is formed from a spunbonded web having a basis weight of about 30 gsm.

Besides the above-mentioned members, the absorbent core 44 may also include a composite absorbent member (not shown), such as a coform material. In this instance, fluids may be wicked from the transfer delay member into the composite absorbent member. The composite absorbent member may be formed separately from the intake member and/or transfer delay member, or may be formed simultaneously therewith. In one embodiment, for example, the composite absorbent member may be formed on the transfer delay member or intake member, which acts a carrier during the coform process described above.

Regardless of its particular construction, the absorbent article 20 typically contains an adhesive for securing to an undergarment. An adhesive may be provided at any location of the absorbent article 20, such as on the lower surface of the backsheet 42. In this particular embodiment, the backsheet 42 carries a longitudinally central strip of garment adhesive 54 covered before use by a peelable release liner 58, which may be formed in accordance with the present invention. Each of the flaps 24 may also contain an adhesive 56 positioned adjacent to the distal edge 34 of the flap 24. A peelable release liner 57, which may also be formed in accordance with the present invention, may cover the adhesive 56 before use. Thus, when a user of the sanitary absorbent article 20 wishes to expose the adhesives 54 and 56 and secure the absorbent article 20 to the underside of an undergarment, the user simply peels away the liners 57 and 58 and disposed them in a water-based disposal system (e.g., in a toilet).

Although various configurations of a release liner have been described above, it should be understood that other release liner configurations are also included within the scope of the present invention. Further, the present invention is by no means limited to release liners and the water-sensitive biodegradable film may be incorporated into a variety of different components of an absorbent article. For example, referring again to FIG. 2, the backsheet 42 of the napkin 20 may include the water-sensitive film of the present invention. In such embodiments, the film may be used alone to form the backsheet 42 or laminated to one or more additional materials, such as a nonwoven web. The water-sensitive biodegradable film of the present invention may also be used in applications other than absorbent articles. For example, the film may be employed as an individual wrap, packaging pouch, or bag for the disposal of a variety of articles, such as food products, absorbent articles, etc. Various suitable pouch, wrap, or bag configurations for absorbent articles are disclosed, for instance, in U.S. Pat. Nos. 6,716,203 to Sorebo. et al. and 6,380,445to Moder, et al., as well as U.S. Patent Application Publication No. 2003/0116462 to Sorebo, et al., all of which are incorporated herein in their entirety by reference thereto for all purposes.

The present invention may be better understood with reference to the following examples.

TEST METHODS

Tensile Properties:

The strip tensile strength values were determined in substantial accordance with ASTM Standard D-5034. A constant-rate-of-extension type of tensile tester was employed. The tensile testing system was a Sintech Tensile Tester, which is available from Sintech Corp. of Cary, N.C. The tensile tester was equipped with TESTWORKS 4.08B software from MTS Corporation to support the testing. An appropriate load cell was selected so that the tested value fell within the range of 10-90% of the full scale load. The sample was held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run at a 300-millimeter per minute rate with a gauge length of 18.0 millimeters and a break sensitivity of 40%. Five samples were tested by applying the test load along the machine-direction and five samples were tested by applying the test load along the cross direction. During the test, samples were stretched at a crosshead speed of 5.0 inches per minute until breakage occurred. The modulus, peak stress, peak strain (i.e., % strain at peak load), and the energy to peak were measured.

Water Disintegration Test:

The rate of film disintegration in tap water was tested using a "slosh box", which has a physical dimension of a 14"×18"×12" high plastic box on a hinged platform. One end of the platform is attached to the reciprocating cam. The typical amplitude is ±2" (4" range), with sloshing occurring at 0.5~1.5 sloshes per second. The preferred action is 0.9~1.3 sloshes per second. During a test, the slosh box rocks up and down with the water inside, "sloshing" back and forth. This action produces a wave front and intermittent motion on a sample susceptible to dispersing in water. To quantify a measurement of sample film disintegration in water, without image analysis, simply timing is sufficient. Three liters of tap water were added into the slosh box and resulted in ~5.5" water depth in the box. A frequency of 3.5 was selected for the testing. Each film sample was cut into 1"×3" size. Three pieces were dropped into the slosh box. The time to disintegrate the sample under the defined conditions was recorded twice for each sample. The average of the time to the sample disintegration is then reported.

and was adjusted to achieve the desired ratio of the plasticizer to starch in the final composition. A vent was also provided at zone 9 to release steam generated due to the presence of the added water in the plasticizer and inherent moisture in the starch. The temperature profile for zones 1 to 10 was 50° C., 80° C., 100° C., 140° C., 140° C., 140° C., 120° C., 100° C., 80° C., and 60° C., respectively. The screw speed was set at 170 rpm.

The extruded potato TPS strand contained 70 wt. % starch (a mixture of 99 wt. % potato starch and 1 wt. % Excel P-40S) and 30 wt. % plasticizer. The strand was smooth, but a die swell was observed. It cooled down through a cooling belt (Bondine Electric Co., Chicago, Ill.). A pelletizer (Emerson Industrial Controls, Grand Island, N.Y.) was used to cut the strand to produce thermoplastic starch pellets, which were then collected and sealed in a bag.

To make blends, the potato TPS was compounded with an Ecoflex® F BX 7011 resin (BASF, Florham Park, N.J.) using the Prism USALAB 16 Twin Screw Extruder described above. The barrel temperatures from zones 1 to 10 were 100° C., 140° C., 150° C., 170° C., 180° C., 180° C., 170° C., 150° C., 140° C., and 130° C., respectively. The screw speed was set at 170 rpm. The strand from the die was pelletized. Three samples were formed using a blown (Sample 1) or casting (Samples 2-3) technique from the pellets (as listed in Table 1). A Rheomix TW100 extruder (Thermal Fisher Scientific of Newington, N.H.) equipped with either a 8" casting film die (for cast films) or a 1" inch annular blown film die (for blown film), as well as metering pump (HAAKE MP1) was employed. The temperature profile for the extruder (zones 1-3), the metering pump (zone 4), and the die (zone 5) was 120° C., 130° C., 130° C., 120° C., and 120° C., respectively. The melt temperature was about 145° C. and the screw speed was 60 rpm.

Various mechanical properties of the film were then tested. The results are set forth below in Table 1.

TABLE 1

Mechanical Properties of Potato TPS/Ecoflex ® Films

| Sample | Ecoflex ® (wt. %) | Potato TPS (wt. %) | Film Type | Film Thickness (mil) | | Modulus (MPa) | | Strain-at-Break (%) | | Peak Stress (MPa) | | Energy-to-Break (J/cm³) | |
|---|---|---|---|---|---|---|---|---|---|---|---|---|---|
| | | | | MD | CD | MD | CD | MD | CD | MD | CD | MD | CD |
| 1 | 30 | 70 | Blown | 1.3 | 1.2 | 85 | 112 | 97 | 102 | 7 | 9 | 7 | 8 |
| 2 | 30 | 70 | Cast | 1.4 | 1.4 | 200 | 179 | 71 | 52 | 12 | 7 | 8 | 3 |
| 3 | 20 | 80 | Cast | 1.7 | 1.9 | 122 | 139 | 203 | 60 | 9 | 8 | 17 | 4 |

EXAMPLE 1

A thermoplastic potato starch ("Potato TPS") was formed as follows. Initially, a mixture of potato starch (Penford Food Ingredients Co., Englewood, Colo.) and surfactant (Excel P-40S, Kao Corporation, Tokyo, Japan) was made at a ratio of the 99 parts of potato starch to the 1 part of surfactant. The mixture was added to a gravimetric K-Tron feeder (K-Tron America, Pitman, N.J., Model KCM-2) that fed the material into a Prism USALAB 16 Twin Screw Extruder (Thermo Electron Corp., Stone, England) at 2 pounds per hour. The extruder had ten (10) zones designated as numbers 1-10, with zone 1 being located adjacent to the feeder. Zones 1 to 9 contained alternating conveying and kneading sections, while zone 10 contained the die where the polymer melts and is shaped into a strand or film. A plasticizer (mixture of 20 wt. % water and 80 wt. % glycerol) was pumped into zone 1. The pumping rate for the plasticizer was determined using a timer

EXAMPLE 2

A thermoplastic corn starch ("Corn TPS") was formed as follows. Initially, a mixture of corn starch and surfactant (Excel P-40S, Kao Corporation, Tokyo, Japan) was made in a kitchen mixer at a ratio of the 99 parts of potato starch to the 1 part of surfactant. The mixture was added to a gravimetric feeder (K-Tron America, Pitman, N.J., Model KCM-2) that fed the material into a Prism USALAB 16 Twin Screw Extruder (Thermo Electron Corp., Stone, England) at 2 pounds per hour. A plasticizer (mixture of 20 wt. % water and 80 wt. % glycerol) was pumped into zone 1. The pumping rate for the plasticizer was determined using a timer and was adjusted to achieve the desired ratio of the plasticizer to starch in the final composition. A vent was also provided at zone 9 to release steam generated due to the presence of the added water in the plasticizer and inherent moisture in the starch. The temperature profile for zones 1 to 10 was 50° C., 80° C., 100° C., 140° C., 140° C., 140° C., 120° C., 100° C., 80° C., and 60° C., respectively. The screw speed was set at 170 rpm so that the torque fluctuated between 60~75% during the processing. The extruded corn TPS strand contained 70 wt. % starch (a mixture of 99 wt. % potato starch and 1 wt. % Excel P-40S) and 30 wt. % plasticizer. The strand cooled down through a cooling belt (Bondine Electric Co., Chicago, Ill.). A pelletizer (Emerson Industrial Controls, Grand Island, N.Y.) was used to cut the strand to produce thermoplastic starch pellets, which were then collected and sealed in a bag.

To make blends, the corn TPS was compounded with an Ecoflex® F BX 7011 resin (BASF, Florham Park, N.J.) using the Prism USALAB 16 Twin Screw Extruder described above. The barrel temperatures from zones 1 to 10 were 100° C., 140° C., 150° C., 170° C., 180° C., 180° C., 170° C., 150° C., 140° C., and 130° C., respectively. The screw speed was set at 170 rpm. The strand from the die was pelletized as described in Example 1. Two samples (Samples 4-5) were formed using a casting technique. A Rheomix TW100 (Thermal Fisher Scientific of Newington, N.H.) casting line was employed. The temperature profile for the extruder (zones 1-3), the metering pump (zone 4), and the die (zone 5) was 150° C., 160° C., 170° C., 160° C., and 160° C., respectively. The melt temperature was about 153° C. and the screw speed was 60 rpm.

Various mechanical properties of the film were then tested. The results are set forth below in Table 2.

TABLE 2

Mechanical Properties of Corn TPS/Ecoflex ® Films

| Sample | Ecoflex ® (wt. %) | Corn TPS (wt. %) | Film Type | Film Thickness (mil) | | Modulus (MPa) | | Strain-at-Break (%) | | Peak Stress (MPa) | | Energy-to-Break (J/cm³) | |
|---|---|---|---|---|---|---|---|---|---|---|---|---|---|
| | | | | MD | CD | MD | CD | MD | CD | MD | CD | MD | CD |
| 4 | 30 | 70 | Cast | 1.2 | 1.3 | 908 | 168 | 3 | 3 | 21 | 11 | 0.3 | 0.1 |
| 5 | 30 | 80 | Cast | 3.3 | 3 | 1071 | 889 | 4 | 3 | 26 | 22 | 1 | 0.3 |

In comparison with the films of Example 1, the films shown in Table 2 have a higher modulus and peak stress.

EXAMPLE 3

The mechanical properties of the films of Examples 1 and 2 were tested after being soaked in water. Specifically, the films were separately cut into a "dog-bone" and then soaked in tap water for 20 minutes to assess the film property changes. The results are set forth below in Table 3.

TABLE 3

Mechanical Properties of Films after Soaking in Water

| Sample | Film Thickness (mil) | | Modulus (MPa) | | Strain-at-Break (%) | | Peak Stress (MPa) | | Energy-to-Break (J/cm³) | |
|---|---|---|---|---|---|---|---|---|---|---|
| | MD | CD | MD | CD | MD | CD | MD | CD | MD | CD |
| 1 | 1.3 | 1.2 | 59 | 55 | 57 | 39 | 6 | 2 | 2 | 0.7 |
| 2 | 1.4 | 1.4 | 46 | 32 | 269 | 24 | 5 | 3 | 8 | 3 |
| 3 | 1.7 | 1.9 | 21 | 41 | 499 | 31 | 7 | 3 | 24 | 0.6 |
| 4 | 1.2 | 1.3 | 26 | 57 | 386 | 46 | 8 | 4 | 21 | 1.3 |
| 5 | 3.3 | 3 | 5 | 31 | 277 | 130 | 3 | 1 | 4 | 1.2 |

In these particular samples, the films were sensitive to water with a change in mechanical properties, but they did not generally disperse or disintegrate.

EXAMPLE 4

A thermoplastic ester starch ("Ester TPS") was formed as follows. Initially, a mixture of an ester starch (Tapon ND, manufactured by National Starch & Chemical Company, Bridgewater, N.J.) and surfactant (Excel P-40S, Kao Corporation, Tokyo, Japan) was made at a ratio of the 98 parts of starch to 2 parts of surfactant. A plasticizer (mixture of 20 wt. % water and 80 wt. % sorbitol) was also added so that the mixture contained 70 wt. % starch (a mixture of 98 wt. % ester starch and 2 wt. % Excel P-40S) and 30 wt. % plasticizer. A kitchen mixer was used for dry mixing. The mixture was then added to a gravimetric K-Tron feeder (K-Tron America, Pitman, N.J., Model KCM-2) that fed the material into a Prism USALAB 16 Twin Screw Extruder (Thermo Electron Corp., Stone, England) at 2 pounds per hour. The extruder had ten (10) zones designated as numbers 1-10, with zone 1 being located adjacent to the feeder. Zones 1 to 9 contained alternating conveying and kneading sections, while zone 10 contained the die where the polymer melts and is shaped into a strand or film. A vent was provided at zone 9 to release steam generated due to the presence of the added water in the plasticizer and inherent moisture in the starch. The temperature profile for zones 1 to 10 was 50° C., 80° C., 100° C., 140° C., 140° C., 140° C., 120° C., 100° C., 80° C., and 60° C., respectively. The screw speed was set at 170 rpm. The strand cooled down through a cooling belt (Bondine Electric Co., Chicago, Ill.). A pelletizer (Emerson Industrial Controls, Grand Island, N.Y.) was used to cut the strand to produce thermoplastic starch pellets, which were then collected and sealed in a bag.

To make blends, the Ester TPS was compounded with an Ecoflex® F BX 7011 resin (BASF, Florham Park, N.J.) using the Prism USALAB 16 Twin Screw Extruder described above. The barrel temperatures from zones 1 to 10 were 100° C., 140° C., 150° C., 170° C., 180° C., 180° C., 170° C., 150° C., 140° C., and 130° C., respectively. The screw speed was set at 170 rpm. The strand from the die was pelletized for film casting. Various samples were formed using a casting technique to form films having an Ester TPS/Ecoflex® weight ratio 90/10, 80/20, 70/30, and 60/40. A Rheomix TW100 (Thermal Fisher Scientific of Newington, N.H.) casting line was employed. The temperature profile for the extruder (zones 1-3), the metering pump (zone 4), and the die (zone 5) was 140° C., 150° C., 160° C., 150° C., and 150° C., respectively. The melt temperature was about 151° C. and the screw speed was 55 rpm. The film thickness was between about 0.001 to 0.002 inches.

EXAMPLE 5

A thermoplastic hydroxypropylated starch ("HP TPS") was formed as follows. Initially, a mixture of a hydroxypropylated starch (Glucosol 800, manufactured by Chemstar Products Company, Minneapolis, Minn.) and surfactant (Excel P-40S, Kao Corporation, Tokyo, Japan) was made at a ratio of the 98 parts of starch to 2 parts of surfactant. A kitchen mixer was used for mixing. The mixture was then added to a K-Tron feeder (K-Tron America, Pitman, N.J.) that fed the material into a Prism USALAB 16 Twin Screw Extruder (Thermo Electron Corp., Stone, England) at 2 pounds per hour. The extruder had ten (10) zones designated as numbers 1-10, with zone 1 being located adjacent to the feeder. Zones 1 to 9 contained alternating conveying and kneading sections, while zone 10 contained the die where the polymer melts and is shaped into a strand or film. A plasticizer (mixture of 70 wt. % water and 30 wt. % glycerol) was pumped into zone 1. The pumping rate for the plasticizer was determined using a timer and was adjusted to achieve the desired ratio of the plasticizer to starch in the final composition. A vent was also provided at zone 9 to release steam generated due to the presence of the added water in the plasticizer and inherent moisture in the starch. The temperature profile for zones 1 to 10 was 50° C., 80° C., 100° C., 140° C., 140° C., 140° C., 120° C., 100° C., 80° C., and 60° C., respectively. The screw speed was set at 170 rpm.

The extruded HP TPS strand contained 70 wt. % starch (a mixture of 98 wt. % hydroxypropylated starch and 2 wt. % Excel P-40S) and 30 wt. % plasticizer. The strand cooled down through a cooling belt (Bondine Electric Co., Chicago, Ill.). A pelletizer (Emerson Industrial Controls, Grand Island, N.Y.) was used to cut the strand to produce thermoplastic starch pellets, which were then collected and sealed in a bag. To make blends, the HP TPS was compounded with an Ecoflex® F BX 7011 resin (BASF, Florham Park, N.J.) using the Prism USALAB 16 Twin Screw Extruder described above. The barrel temperatures from zones 1 to 10 were 100° C., 140° C., 150° C., 170° C., 180° C., 180° C., 170° C., 150° C., 140° C., and 130° C., respectively. The screw speed was set at 170 rpm. The strand from the die was pelletized. Various samples were formed using a casting technique to form films having an HP TPS/Ecoflex® weight ratio 90/10, 80/20, 70/30, and 60/40. A Rheomix TW100 (Thermal Fisher Scientific of Newington, N.H.) casting line was employed. The temperature profile for the extruder (zones 1-3), the metering pump (zone 4), and the die (zone 5) was 120° C., 130° C., 130° C., 120° C., and 120° C., respectively. The melt temperature was about 145° C. and the screw speed was 70 rpm. The film thickness was about 0.002 inches.

EXAMPLE 6

The mechanical properties of the films of Examples 4 and 5 were tested. Specifically, the film samples were cut into "dog-bone" shapes with a center width of 3.0 millimeters and subjected to the tensile test described above. The results are set forth below Tables 4-5.

TABLE 4

Mechanical Properties of Ester TPS/Ecoflex ® Films

| Sample | Ecoflex ® (wt. %) | Tapon ND TPS (wt. %) | Film Type | Film Thickness (mil) MD | CD | Modulus (MPa) MD | CD | Strain-at-Break (%) MD | CD | Peak Stress (MPa) MD | CD | Energy-to-Break (J/cm³) MD | CD |
|---|---|---|---|---|---|---|---|---|---|---|---|---|---|
| 6 | 10 | 90 | Cast | 1.1 | NM | 1104 | NM | 2 | NM | 626 | NM | 0.3 | NM |
| 7 | 20 | 80 | Cast | 1.1 | 1 | 980 | 332 | 3 | 2 | 31 | 6 | 0.5 | 0.1 |
| 8 | 30 | 70 | Cast | 1 | 1 | 1363 | 203 | 5 | 1 | 45 | 6 | 2 | 0.1 |
| 9 | 40 | 60 | Cast | 0.7 | 0.8 | 1380 | 287 | 6 | 2 | 47 | 6 | 2 | 0.1 |

ND = not measured

TABLE 5

Mechanical Properties of HP TPS/Ecoflex ® Films

| Sample | Ecoflex ® (wt. %) | Glucosol 800 TPS (wt. %) | Film Type | Film Thickness (mil) MD | CD | Modulus (MPa) MD | CD | Strain-at-Break (%) MD | CD | Peak Stress (MPa) MD | CD | Energy-to-Break (J/cm³) MD | CD |
|---|---|---|---|---|---|---|---|---|---|---|---|---|---|
| 10 | 0 | 100 | Cast | 1.4 | 2.2 | 740 | 196 | 6 | 6 | 29 | 5 | 1 | 0.1 |
| 11 | 10 | 90 | Cast | 1.2 | 1.1 | 665 | 646 | 34 | 4 | 22 | 19 | 6 | 0.4 |
| 12 | 20 | 80 | Cast | 1.1 | 1.1 | 901 | 221 | 30 | 2 | 28 | 5 | 7 | 0.1 |
| 13 | 30 | 70 | Cast | 1.2 | 1.2 | 702 | 505 | 50 | 3 | 23 | 13 | 10 | 0.1 |
| 14 | 40 | 60 | Cast | 1.1 | 1 | 720 | 476 | 95 | 3 | 24 | 13 | 20 | 0.3 |

As indicated, increasing the amount of Ecoflex® in the Ester TPS/Ecoflex® films generally increased the modulus, peak stress, elongation, and energy to break. It should be noted that modulus data could not be obtained for the CD of the 90/10 Ester TPS/Ecoflex® samples because they broke when being cut for testing. Further, increasing the amount of Ecoflex® in the HP TPS/Ecoflex® films generally increased the elongation and energy to break. Overall, the HP TPS films had a lower moduli than the Ester TPS films, which may indicate that glycerol performed better as a plasticizer than sorbitol.

In addition to undergoing tensile testing, the samples of Examples 4 and 5 were also subjected to the above-described water disintegration test. After 30 seconds in tap water, the HP TPS/Ecoflex® (90/10 and 80/20) and Ester TPS/Ecoflex® (80/20 and 90/10) films visibly disintegrated in tap water. The HP TPS/Ecoflex® (60/40) film did not exhibit visible disintegration even after 30 minutes in tap water. Thus, at a low level of the biodegradable polyester (e.g., 10 wt. %), the film was generally water-dispersible. At levels above 20 wt. %, however, the film tended to become less water-dispersible.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article comprising a water-sensitive biodegradable film, wherein the absorbent article comprises a body portion that includes a liquid permeable topsheet, a generally liquid impermeable backsheet, and an absorbent core positioned between the backsheet and the topsheet, further comprising a release liner that defines a first surface and an opposing second surface, the first surface being disposed adjacent to an adhesive located on the absorbent article, wherein the backsheet, the release liner, or both includes the water-sensitive biodegradable film, the film comprising:

from 1 wt. % to 20 wt. % of a biodegradable polyester component, wherein the biodegradable polyester component includes at least one biodegradable aliphatic-aromatic copolyester that has a melting point of from about 50° C. to about 180° C. and a glass transition temperature of about 0° C. or less; and from 80 wt. % to 99 wt. % of a thermoplastic starch component, comprising from about 60 wt. % to about 80 wt. % of at least one water-soluble, chemically modified starch, from about 0.5 wt. % to about 4 wt. % of at least one surfactant, and from about 20 wt. % to about 40 wt. % of at least one plasticizer, wherein the water-soluble, chemically modified starch comprises a starch ester, a hydoxyalkyl starch, or a combination thereof;

wherein the film has a thickness of about 50 micrometers or less and exhibits visible disintegration when sloshed in tap water for 30 seconds at a frequency of 3.5 sloshes per second, the film further exhibiting a dry ultimate tensile strength of from about 20 to about 50 Megapascals in the machine direction and a dry modulus of elasticity of from about 400 to about 1000 Megapascals in the machine direction.

2. The absorbent article of claim 1, wherein the biodegradable aliphatic-aromatic copolyester has a number average molecular weight of from about 40,000 to about 120,000 grams per mole.

3. The absorbent article of claim 1, wherein the biodegradable aliphatic-aromatic copolyester has a glass transition temperature of about −10° C. or less.

4. The absorbent article of claim 1, wherein the biodegradable aliphatic-aromatic copolyester has a melting point of about 80° C. to about 160° C.

5. The absorbent article of claim 1, wherein the plasticizer is a polyhydric alcohol.

6. The absorbent article of claim 5, wherein the plasticizer is a sugar alcohol.

7. The absorbent article of claim 1, wherein the surfactant is a nonionic surfactant having an HLB value of from about 1 to about 10.

8. The absorbent article of claim 7, wherein the nonionic surfactant includes monoglyceride and/or diglyceride of a fatty acid.

9. The absorbent article of claim 1, wherein the film has a thickness of from about 5 to about 30 micrometers.

10. The absorbent article of claim 1, wherein the film exhibits a dry ultimate tensile strength of from about 5 to about 30 Megapascals in the cross-machine direction and a dry modulus of elasticity of from about 150 to about 500 Megapascals in the cross-machine direction.

* * * * *